United States Patent
Cipolletti et al.

(10) Patent No.: US 8,124,758 B2
(45) Date of Patent: Feb. 28, 2012

(54) PROCESS FOR THE PREPARATION OF N-ACETYL-D-MANNOSAMINE MONOHYDRATE

(75) Inventors: Giovanni Cipolletti, Milan (IT); Giancarlo Tamerlani, Bologna (IT); Ilaria Lombardi, Montecatini Terme (IT); Debora Bartalucci, Vinci (IT)

(73) Assignee: Inalco S.p.A., Milan (IT)

( * ) Notice: Subject to any disclaimer, the term of this patent is extended or adjusted under 35 U.S.C. 154(b) by 501 days.

(21) Appl. No.: 12/227,423

(22) PCT Filed: May 18, 2007

(86) PCT No.: PCT/EP2007/054813
§ 371 (c)(1), (2), (4) Date: Nov. 14, 2008

(87) PCT Pub. No.: WO2007/135086
PCT Pub. Date: Nov. 29, 2007

(65) Prior Publication Data
US 2009/0131654 A1    May 21, 2009

(30) Foreign Application Priority Data
May 19, 2006 (IT) .............. MI2006A0991

(51) Int. Cl.
*C07H 1/06* (2006.01)

(52) U.S. Cl. .................................... 536/127
(58) Field of Classification Search .......... 536/127
See application file for complete search history.

(56) References Cited

U.S. PATENT DOCUMENTS
4,349,542 A * 9/1982 Staniforth ............ 424/679
6,156,544 A * 12/2000 Dawson et al. ........... 435/84

OTHER PUBLICATIONS
Spivak et al, J. Am. Chem. Soc., 1959, 81 (10), pp. 2403-2404).*
* cited by examiner

*Primary Examiner* — Elli Peselev
(74) *Attorney, Agent, or Firm* — Abelman, Frayne & Schwab

(57) ABSTRACT

A process is described for the preparation of N-Acetyl-D-mannosamine monohydrate of formula (I) a specific intermediate in the synthesis of N-Acetyl-neuraminic acid, that is an important starting product for the synthesis of various pharmaceutically active products.

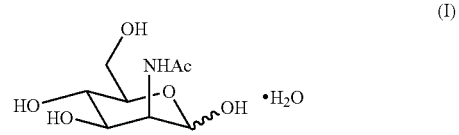

(I)

15 Claims, No Drawings

PROCESS FOR THE PREPARATION OF N-ACETYL-D-MANNOSAMINE MONOHYDRATE

FIELD OF INVENTION

The present invention relates to the field of the synthesis of sugars, and in particular to a process for the preparation of N-Acetyl-D-mannosamine monohydrate having the formula (I) reported hereinafter.

PRIOR ART

N-Acetyl-D-mannosamine is an intermediate specific for the synthesis of N-Acetyl-neuraminic [A1] acid that, in its turn, is the starting material useful for the synthesis of various active ingredients, especially of antiviral products.

The N-Acetyl-neuraminic acid is a sialic acid existing as a component of mucolipids and mucoproteins, and as a component of oligosaccharides that can be found, for example, in milk in small quantities.

Therefore, there is the need to produce the N-Acetyl-neuraminic acid, by synthesis way and, therefore, to have a great availability of products such as N-Acetyl-D-mannosamine, from which the acid is obtained.

Up today various methods for the synthesis of N-Acetyl-D-mannosamine, either by enzymatic, or fermentative or chemical way are described in the literature.

Among the methods of enzymatic synthesis it is well-known, for example, the interconversion from N-Acetyl-D-glucosamine to N-acetyl-D-mannosamine using N-Acetyl-D-glucosammine-2-epimerase, as reported for example by Lee, Jeong-Oh et al. In *Enzyme and Microbial Technology* 2004, 35 (2-3), 121-125.

In the International Patent Application No. WO 00/52138, is instead reported an example of synthesis of N-Acetyl-D-mannosamine by fermentation with *Klebsiella pneumoniae* using N-Acetyl-D-glucosamine as substrate.

Among the methods of chemical synthesis in the literature is reported the alkaline epimerisation of N-Acetyl-D-glucosamine at pH>9 using different bases such as sodium or potassium hydroxide or a ionic exchange resin such as Duolite® A113, as described in the International Patent Application No. WO 94/29476. Other similar methods of chemical synthesis which use other bases such as calcium hydroxide or a basic resin, are also described in literature.

A different chemical synthetic method is described in Mack, Hans et al. *Carb. Res.*, 1988, 175(2), 311-16 which consists in the cyclisation of the 2-Acetamide-2-deoxy-D-glucopyranoside product to oxazoline derivative, the subsequent hydrolysis to 2-Acetamide-2-deoxy-5,6-O-isopropylidene-D-glucofuranose and the isomerisation by treatment with Amberlite® IRA-68 basic resin to 2-Acetamide-2-deoxy-D-mannose. This method takes lot of time, is laborious and hard to be industrially exploited.

A further chemical synthesis of N-Acetyl-D-mannosamine is described in the European Patent No. 0 385 287; this synthesis requires the reaction of the N-Acetyl-D-glucosamine derivative with a phosphorous ylide (reaction of Wittig) and epimerisation to the corresponding olefinic derivative which is then oxidised with ozone to mannosamine derivative. This process requires the use of reagents and solvents that make it hard to be scaled up.

Moreover, any chemical synthesis known to the Applicant of N-Acetyl-D-mannosamine from N-Acetyl-D-glucosamine yields as the final product not the pure N-Acetyl-D-mannosamine, but a sugars mixture enriched in N-Acetyl-D-mannosamine which remains in the solution together with the reaction impurities and with a substantial amount of N-Acetyl-D-glucosamine.

Therefore, the need is still felt to have available a chemical preparation process of N-Acetyl-D-mannosamine, that can be industrially scaled up and that is suitable for the preparation of this sugar with a high purity degree.

SUMMARY OF THE INVENTION

Now the Applicant has found a process for the preparation of N-Acetyl-D-mannosamine monohydrate having the formula (I) herein below reported, that is particularly simple and economic, and allow to overcome the disadvantages above mentioned for the known processes, by synthesising N-Acetyl-D-mannosamine monohydrate in crystalline form with a purity higher than 98%.

It is therefore subject of the present invention a process for the preparation of N-Acetyl-D-mannosamine monohydrate in crystalline form with a purity higher than 98% having the formula (I)

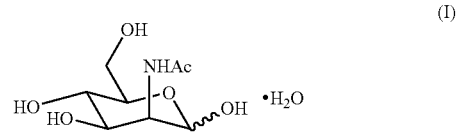

said process comprising the selective crystallisation by seeding a mixture of N-Acetyl-D-glucosamine and N-Acetyl-D-mannosamine with N-Acetyl-D-mannosamine monohydrate.

A further subject of the invention is the use of N-Acetyl-D-mannosamine monohydrate obtained by the above said process, for the preparation of N-Acetyl-neuraminic acid.

The features and advantages of the present process will be better described in the following detailed description.

DETAILED DESCRIPTION OF THE INVENTION

In the following description the abbreviations NAG, NAM and NANA will be used to respectively indicate the compounds N-Acetyl-D-glucosamine, N-Acetyl-D-mannosamine and N-Acetyl-neuraminic acid.

The NAM monohydrate used as seed material in the present process can be obtained, for example, by following the preparation procedure described in Chava Telem Spivak et al. *J. Am. Chem. Soc. Vol.* 81, 2403-2404.

According to a preferred embodiment of the present process, the seeding is carried out by adding a quantity of NAM monohydrate comprised between 0.5% and 5% by weight in respect to the total weight of NAG and NAM in the starting mixture, and filtrating the so obtained solid product after a time comprised between 0.5 and 2 hours.

Optimal results in terms of purity of NAM monohydrate, are obtained with a quantity of the seed material equal to 2.6% by weight with respect to the total weight of NAG and NAM in the starting mixture, and filtrating the solid product obtained, after a time of 1 hour and 50 minutes from the seeding.

The starting mixture preferably consists of a mixture of NAG and NAM wherein the molar ratio NAG:NAM is comprised between 55:45 and 90:10; this mixture is preferably suspended in a n-propanol:water mixture having a volume ratio between 80:20 and 90:10, and the so obtained suspension is optionally subjected to warm filtration before the seeding.

According to a preferred embodiment of the present process, the starting mixture of NAG and NAM is obtained by base-catalysed epimerisation of NAG until the epimerisation balance between NAG and NAM is achieved, followed by two subsequent crystallisation steps of non reacted NAG, finally obtaining a mixture of NAM and NAG on which a selective crystallisation is carried out by seeding.

The above said epimerisation reaction of NAG can be carried out, for example, in water at a temperature comprised between 30 and 80° C., and preferably at the temperature of 60° C., using as base an organic base selected, for example, from the group consisting of Triethylamine, Diisopropylamine, N-Ethylbutylamine, N,N,N,N-Tetramethylethylendiamine, N-Methylpiperazine and diethanolamine. The preferred base of the invention is Triethylamine.

The quantity of water in which the starting NAG is suspended is typically the minimum quantity necessary to bring NAG in suspension, equal to 1.6 volumes; the quantity of organic base added is, for example, between 0.5 and 10% by moles with respect to the moles of the starting NAG, and preferably equal to 2.3%. The so obtained aqueous suspension of NAG is therefore warmed up at a temperature between 30 and 80° C. for the time necessary to reach the epimerisation balance, corresponding to a NAM/(NAM+NAG) ratio of approximately 20.

Once the epimerisation balance is obtained as above described, a first crystallisation of non reacted NAG can be carried out, for example, by neutralising the base used to catalyse the epimerisation reaction with a suitable quantity of acid, preferably acetic acid, and by concentrating the reaction mixture until a thick precipitate is obtained by slow cooling, from this precipitate a first portion of NAG is crystallised and recovered by filtration.

Then the second crystallisation is carried out on the NAG-depleted filtrate by concentrating the filtrate and adding a suitable seed of NAG to obtain a second NAG portion which is then recovered by filtration.

Both NAG portions are preferably washed with n-propanol:water mixtures having a ratio between 80:20 and 90:10, and/or with n-propanol, and the washings are added to the filtrate before the subsequent crystallisation.

The filtrate obtained from the second crystallisation of NAG consists therefore of a mixture of NAG and NAM in a mixture of water and n-propanol, that can be subjected to the selective crystallisation of the present process by seeding, to obtain the desired NAM in crystalline form, with a purity higher than 98% as described above.

Preferably, before the seeding, the filtrated product is warmed up at 65° C. to eliminate possible crystals of NAG, then quickly cooled at a temperature between 18 and 22° C., and preferably at 20° C.

Once the NAM monohydrate is recovered by filtration, concentration of the filtrated product and cooling, for example for 16 hours at 2° C., a mixture of NAM:NAG approximately 45:55 is obtained, that can be used in a further cycle.

Besides the high purity of the obtained NAM monohydrate, the present process as above described, has further considerable advantages: the final product has a high yield compared to the product in the reaction mixture, higher than 70%, and besides having a low NAG content, it does not contain those great quantities of by-products that are instead found in the products obtained according to the prior art processes.

Furthermore, the process of the is also easily industrially exploitable since the epimerisation reaction is carried out in water and the organic base is used in catalytic quantities.

The NAM monohydrate in crystalline form and having high purity, obtained according to the present process, can be used without further purification steps, for the preparation of NANA according to one of the procedures known in the prior art, for example according to the procedure described in WO 94/29476 in which NAM is incubated with sodium pyruvate in presence of NANA-aldolase enzyme.

The following non-limiting example of the present invention is given by way of illustration.

EXAMPLE 1

Synthesis of NAM Monohydrate

Compound of Formula I 6.67 kg of water are loaded in a 10 litres cleaned reactor and they are put under stirring. Then 4 Kg of NAG are loaded and warmed up at 60±2° C.; 60 ml of Triethylamine are added and kept at the temperature of 60±2° C. for two hours. Afterwards 31 ml of glacial acetic acid are added and a sample for the HPLC analysis is drawn, from which it comes out it has been achieved the ratio 80/20 between NAG and NAM, thereafter the reaction mixture is concentrated under vacuum at an internal temperature lower than 60° C. discharging 4.6 litres of water. The temperature is brought to 60±3° C. and maintained for 30 minutes; thereafter, with a gradient of around 10° C./h, it is cooled down to 20±3° C.

A centrifugation step is performed and the centrifuged syrup is uploaded and stocked aside from the washings.

A first washing is carried out with 1.09 litres of a mixture n-propanol/demineralised water in a ratio of 85/15 and a second washing with 1.640 ml of n-propanol.

2.421 g of NAG are obtained from the first recovery. The centrifuged syrup is further concentrated till a residue of 2 Kg is obtained.

To the syrup so concentrated the NAG washings of the first recovery are added and then the mixture is warmed up at 60° C. A precipitation of a second recovery of NAG can take place and, in case that no precipitation takes place at 60° C., it is seeded with 0.5% of NAG compared to the quantity used in the epimerisation and all is maintained under stirring at 60±2° C. for 1 hour. The solid is filtrated and washed with a mixture 85/15 n-propanol/water (180 ml) and, thereafter, with 360 ml of n-propanol. 220 g of NAG from second recovery are recovered. The filtrated is warmed at 65±2° C., thereafter it is quickly cooled down to 20° C. and it is seeded with 11 g of NAM monohydrate. After 1 hour and 50 minutes it is filtrated and washed with 550 ml of 85/15 n-propanol/water mixture. The solid obtained under vacuum is dehydrated at 40° C. till a steady dry weight.

278 g of NAM are obtained (without counting the amount of the seed they are 267 g) having a HPLC purity higher than 98%.

The mother-liquid have been concentrated till a residue of 2,174 g, cooled down to room temperature and after 12 hours at room temperature and 5 hours under stirring at 3±2° C., the solid has been filtrated, washed with n-propanol (700 ml) and dehydrated. A mixture of NAM monohydrate (335 g) and of NAG (300 g) is obtained, the same is suspended in filtration and washing mother-liquid of a subsequent NAM (see Example 2).

$^1$H-NMR (DMSO, 300 MHz): δ ppm 7.15, 6.55, 4.78, 4.69-4.66 (40H), 4.38, 4.16, 3.75-3.64, 3.55-3.40 (m, 5H), 3.24, 3.14-3.02 (m, 2H), 1.89 (s, 3H, NHCOCH$_3$)

$^{13}$C-NMR (DMSO, 300 MHz): δ ppm 170.79 (NH-COCH$_3$), 93.47 (C-1), 77.47, 72.59, 67.08, 61.32, 54.05 (C-2, C-3, C-4, C-5, C-6) 23.01 (NHCOCH$_3$).

EXAMPLE 2

Synthesis of NAM Monohydrate

Compound of Formula I 6.29 kg of water are loaded in a 10 litres cleaned reactor and put under stirring. Thereafter 3.78 Kg of NAG are loaded and warmed up at 60±2° C.; 56.5 ml of Triethylamine are added and kept at the temperature of 60±2° C. for two hours. Afterwards 29.2 ml of glacial acetic acid are added and a sample for the HPLC analysis is drawn, from which it is found that the ratio 80/20 between NAG and NAM is achieved, thereafter the reaction mixture is concentrated under vacuum at an internal temperature lower than 60° C. until a residue of 5.1 Kg is obtained.

The temperature is brought to 60±3° C. and kept at said degree for 30 minutes; thereafter, with a gradient of around 10° C./h, it is cooled down to 20±3° C.

A centrifugation step is performed and the centrifuged syrup is uploaded and stocked aside from the washings.

A first washing is carried out with 1.04 litres of a mixture n-propanol/demineralised water 85/15 and a second washing with 1,550 ml of n-propanol.

2,510 g of NAG are obtained from the first recovery. The centrifuged syrup is further concentrated till a residue of 1,650 g is obtained. The NAG washings of the first recovery are added to the syrup so concentrated and all is warmed up at 60° C., obtaining the precipitation of a second recovery of NAG. Thereafter, it is seeded with 0.5% of NAG compared to the quantity used in the epimerisation and it is kept under stirring at 60±2° C. for 1 hour.

The solid is filtrated and washed with a mixture n-propanol/water 85/15 (150 ml) and, thereafter, with 340 ml of n-propanol. 64 g of NAG from second recovery are recovered. The filtrated is warmed at 65±2° C., then it is quickly cooled down to 20° C. and it is seeded with 10 g of NAM monohydrate. After 1 hour and 50 minutes it is filtrated and washed with 530 ml of a n-propanol/water mixture 85/15. The solid obtained under vacuum is dehydrated at 40° C. till a steady dry weight. 465 g of NAM are obtained (without counting the amount of the seed they are 455 g) having a HPLC purity higher than 98%.

The mother liquids are added with the product recovered from the previous test (see EXAMPLE 1) consisting of 335 g of NAM and 300 g of NAG. They are warmed up at 55±2° C., they are filtered washing the solid with 180 ml of a n-propanol/water 85/15 mixture and, afterwards, with 300 ml of n-propanol. 280 g of NAG are obtained from the third recovery.

The mother liquids are cooled down to 20° C. and are seeded with 10 g of NAM. The suspension is kept under stirring at 20±2° C. for 2 hours and, afterwards, it is filtrated and the obtained is washed obtaining 316 g of NAM (without counting the amount of the seed they are 306 g) having a HPLV purity higher than 98%.

The collected mother liquids are added to the washings of NAG from the first recovery and have been concentrated till a residue of 1,884 g is obtained. All it has been left under stirring for 12 hours at room temperature and after it is cooled for 2 hours. The solid has been filtrated, washing it with 400 ml of n-propanol. 509 g of a mixing of NAG (45%) and NAM (56%) are obtained.

EXAMPLE 3

Synthesis of NAM Monohydrate

Compound of Formula I 27.6 Kg of water are loaded in a cleaned 100 litres-reactor and they are put under stirring. Thereafter 16.8 Kg of NAG are loaded and warmed up at 60±2° C.; 248 ml of Triethylamine are added and kept at the temperature of 60±2° C. for two hours. Afterwards 128 ml of glacial acetic acid are added and a sample is drawn for the HPLC analysis. From the HPLC analysis it is found that the ratio 80/20 between NAG and NAM is achieved, then the reaction mixture is concentrated under vacuum at an internal temperature lower than 60° C. discharging 19.3 litres of water.

The temperature is brought to 60±3° C. and kept at said degree for 30 minutes, then, with a gradient of around 10° C./h, it is cooled down to 20±3° C.

A centrifugation step is performed and the centrifuged syrup is uploaded and stocked aside from the washings.

A first washing is carried out with 4.6 litres of a n-propanol/demineralised water 85/15 mixture and a second washing with 6.9 litres of n-propanol. The centrifuged syrup is further concentrated discharging 4.1 litres of water. The NAG washings of the first recovery are added to the syrup so concentrated and all is warmed up at 60° C.

In this case, at the temperature of 60° C., there was no precipitation of a second recovery of NAG but a seeding is however carried out with 0.5% of NAG compared to the quantity used in the epimerisation step and it is kept under stirring at 60±2° C. for 1 hour.

The solid is filtered and washed with a n-propanol/water 85/15 mixture (2,310 ml). The filtrated is warmed at 65±2° C., thereafter it is quickly cooled down to 20° C. and it is seeded with 46 g of NAM monohydrate. After 1 hour and 50 minutes it is filtrated and washed with 2.5 litres of a 85/15 n-propanol/water mixture. The solid obtained under vacuum is dehydrated at 40° C. till a steady dry weight.

1.5 Kg of NAM are obtained having a HPLC purity higher than 98%. The yield of first recovery of NAM is on the average of 8.9±2.5. The mother liquids have been concentrated till a residue of approximately 8 litres is obtained and the concentrated solution was cooled to room temperature.

After 12 hours at room temperature and 5 hours under stirring at 3±2° C., the solid has been filtrated, washed with n-propanol (3 litres) and dehydrated. It is obtained a mixture of NAM monohydrate (45%5%) and NAG (55±5%) which can be reprocessed as above described in Example 2.

EXAMPLE 4

Synthesis of NAM Monohydrate

Compound of Formula I 82 g of water are loaded in a 250 ml-flask with 4 necks and they are put under stirring. 50 g of NAG are loaded and warmed at 60±2° C., 0.75 ml of Diisopropylamine are added and kept at the temperature of 60±2° C. for 3 hours. The reaction is followed by the HPLC analysis. After 3 hours the NAM/(NAM+NAG) ratio is 21.6.

The NAM is then isolated as above described in Example 1.

EXAMPLE 5

Synthesis of NAM Monohydrate

Compound of Formula I 82 g of water are loaded in a 250 ml-flask with 4 necks and they are put under stirring. 50 g of NAG are loaded and warmed at 60±2° C., 0.75 ml of N-EthylButylamine are added and kept at the temperature of 60±2° C. for 3 hours.

The reaction is followed by the HPLC analysis. After 3 hours the NAM/(NAM+NAG) ratio is 19.5.

The NAM is then isolated as above described in Example 1.

EXAMPLE 6

Synthesis of NAM Monohydrate

Compound of Formula I 82 g of water are loaded in a 250 ml-flask with 4 necks and they are put under stirring. 50 g of NAG are loaded and warmed at 70±2° C.; 0.8 ml of N,N,N,N-TetraMethylEthylendiamine are added and kept at the temperature of 70±2° C. for 3 hours. The reaction is followed by the HPLC analysis. After 3 hours the NAM/(NAM+NAG) ratio is 21.2.

The NAM is then isolated as above described in Example 1.

EXAMPLE 7

Synthesis of NAM Monohydrate

Compound of Formula I 82 g of water are loaded in a 250 ml-flask with 4 necks and they are put under stirring. 50 g of NAG are loaded and warmed at 70±2° C.; 0.6 ml of N-Methylpiperazine are added and kept at the temperature of 70±2° C. for 3 hours. The reaction is followed by the HPLC analysis. After 3 hours the NAM/(NAM+NAG) ratio is 18.9.

The NAM is then isolated as above described in Example 1.

EXAMPLE 8

Synthesis of NAM Monohydrate

Compound of Formula I 82 g of water are loaded in a 250 ml-flask with 4 necks and they are put under stirring. 50 g of NAG are loaded and warmed at 80±2° C.; 0.6 ml of N-Methylpyperazine are added and kept at the temperature of 80±2° C. for 3 hours. The reaction is followed by the HPLC analysis. After 3 hours the NAM/(NAM+NAG) ratio is 20.8.

The NAM is then isolated as above described in Example 1.

EXAMPLE 9

Synthesis of NAM Monohydrate

Compound of Formula I 82 g of water are loaded in a 250 ml-flask with 4 necks and they are put under stirring. 50 g of NAG are loaded and warmed at 80±2° C.; 0.5 ml of Diethanolamine are added and kept at the temperature of 80±2° C. for 3 hours. The reaction is followed by the HPLC analysis. After 3 hours the NAM/(NAM+NAG) ratio is 21.6.

The NAM is then isolated as above described in Example 1.

EXAMPLE 10

Synthesis of NAM Monohydrate

Compound of Formula I 82 g of water are loaded in a 250 ml-flask with 4 necks and they are put under stirring. 50 g of NAG are loaded and warmed at 50±2° C.; 0.75 ml of Triethylamine are added and kept at the temperature of 50±2° C. for 7 hours. The reaction is followed by the HPLC analysis. After 7 hours the NAM/(NAM+NAG) ratio is 19.6. The NAM is then isolated as above described in Example 1.

The invention claimed is:

1. A process for the preparation of N-Acetyl-D-mannosamine monohydrate in crystalline form with a purity higher than 98% having the formula (I)

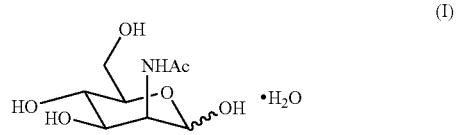

said process comprising the selective crystallisation by seeding a starting mixture of N-Acetyl-D-glucosamine and N-Acetyl-D-mannosamine with N-Acetyl-D-mannosamine monohydrate; wherein said starting mixture consists in a mixture of N-Acetyl-D-glucosamine and N-Acetyl-D-mannosamine wherein the molar ratio Acetyl-D-glucosamine: N-Acetyl-D-mannosamine is comprised between 55:45 and 90:10.

2. The process according to claim 1, wherein said seeding is carried out by adding a quantity of N-Acetyl-D-mannosamine monohydrate between 0.5% and 5% by weight with respect to the total weight of N-Acetyl-D-glucosamine and N-Acetyl-D-mannosamine in the starting mixture, and filtrating the so obtained solid product after a time comprised between 0.5 and 2 hours.

3. The process according to claim 1, wherein said seeding is carried out by adding a quantity of monohydrate N-Acetyl-D-mannosamine of 2.6% by weight with respect to the total weight of N-Acetyl-D-glucosamine and N-Acetyl-D-mannosamine in the starting mixture and filtrating the so obtained solid product after a time of 1 hour and 50 minutes from the seeding.

4. The process according to claim 1, wherein said mixture of N-Acetyl-D-glucosamine and N-Acetyl-D-mannosamine is suspended in a mixture of n-propanol:water having a volume ratio between 80:20 and 90:10, and it is subjected to an optional warm filtration before the seeding.

5. The process according to claim 1, wherein said mixture of N-Acetyl-D-glucosamine and N-Acetyl-D-mannosamine is obtained by base-catalysed epimerisation of N-Acetyl-D-glucosamine until the epimerisation balance between N-Acetyl-D-glucosamine and N-Acetyl-D-mannosamine is achieved, followed by two subsequent crystallisation steps of non reacted N-Acetyl-D-glucosamine, finally obtaining said mixture of N-Acetyl-D-glucosamine and N-Acetyl-D-mannosamine.

6. The process according to claim 5, wherein said epimerisation is carried out in water at a temperature between 30 and 80° C., in the presence of an organic base.

7. The process according to claim 6, wherein said organic base is selected from the group consisting of Triethylamine, Diisopropylamine, N-Ethylbutylamine, N,N,N,N-Tetramethylethylenediamine, N-Methylpiperazine and Diethanolamine.

8. The process according to claim 6, wherein said organic base is Triethylamine.

9. The process according to claim 6, wherein said epimerisation is carried out by suspending N-Acetyl-D-glucosamine in a quantity of water equal to 1.6 volumes.

10. The process according to claim 6, wherein said organic base is in a quantity comprised between 0.5 and 10% by moles with respect to the moles of N-Acetyl-D-glucosamine.

11. The process according to claim 10, wherein said organic base is in a quantity equal to 2.3% by moles with respect to the moles of N-Acetyl-D-glucosamine.

12. The process according to claim 5, wherein the N-Acetyl-D-glucosamine obtained from said two subsequent crystallisation steps is washed with n-propanol mixtures:water in ratio between 80:20 and 90:10, and/or with n-propanol and the washings of the first crystallisation are added to the filtrate before the subsequent crystallisation.

13. The process according to claim 5, wherein the first of said two subsequent crystallisation steps of non reacted N-Acetyl-D-glucosamine is carried out after neutralisation of the base used to catalysed the epimerisation reaction with a suitable quantity of acid, concentrating the reaction mixture until a thick precipitate is obtained by slow cooling, and from this precipitate a first portion of NAG is crystallised and recovered by filtration.

14. The process according to claim 13, wherein said acid is acetic acid.

15. The process according to claim 5, wherein the second of said two subsequent crystallisation steps of non reacted N-Acetyl-D-glucosamine is carried out by concentrating the filtrate coming from the first of said crystallisation steps, adding the washing of the product of said first crystallisation and by adding a suitable seeding of N-Acetyl-D-glucosamine recovered by filtration.

\* \* \* \* \*